US010524709B2

(12) United States Patent
Harttig

(10) Patent No.: US 10,524,709 B2
(45) Date of Patent: Jan. 7, 2020

(54) LANCET MAGAZINE AND METHOD FOR THE PRODUCTION THEREOF

(71) Applicant: Roche Diagnostics Operations, Inc., Indianapolis, IN (US)

(72) Inventor: Herbert Harttig, Neustadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1842 days.

(21) Appl. No.: 13/669,952

(22) Filed: Nov. 6, 2012

(65) Prior Publication Data

US 2013/0066171 A1   Mar. 14, 2013

Related U.S. Application Data

(63) Continuation of application No. PCT/EP2011/001846, filed on Apr. 13, 2011.

(30) Foreign Application Priority Data

May 6, 2010   (EP) .................................. 10004776

(51) Int. Cl.
*A61B 5/151* (2006.01)
*A61B 5/15* (2006.01)
*A61B 5/157* (2006.01)
*B65B 55/02* (2006.01)

(52) U.S. Cl.
CPC .......... *A61B 5/15151* (2013.01); *A61B 5/157* (2013.01); *A61B 5/150358* (2013.01); *B65B 55/02* (2013.01); *A61B 5/15146* (2013.01)

(58) Field of Classification Search
CPC .......... A61B 5/1117; A61B 5/15146–5/15155; A61B 5/15151; A61B 5/157; A61B 5/150358; B65B 55/02
USPC .................................................. 606/181–183
See application file for complete search history.

(56) References Cited

U.S. PATENT DOCUMENTS

| | | | | |
|---|---|---|---|---|
| 4,719,277 A | * | 1/1988 | Behnke | A61L 2/022 210/500.21 |
| 5,070,886 A | | 12/1991 | Mitchen et al. | |
| 5,304,192 A | | 4/1994 | Crouse | |
| 5,846,422 A | * | 12/1998 | Ditter | B01D 61/14 210/490 |
| 6,270,637 B1 | * | 8/2001 | Crismore | C12Q 1/001 204/403.04 |

(Continued)

FOREIGN PATENT DOCUMENTS

DE   102005003789 A1   7/2006
EP   0951939 B1   10/1999
(Continued)

*Primary Examiner* — Devin B Henson

(57) ABSTRACT

A lancet magazine is disclosed which includes a housing and a plurality of lancets each of which is enclosed in a sterile chamber of the housing, wherein the chambers each have a puncturing opening which is closed with a foil, wherein the lancets include a sample receiving device for receiving body fluid and the chambers each include a further opening which is closed with a membrane that is permeable to gas and fluid and includes a lower side that faces the lancet and serves to receive body fluid from the sample receiving device and an upper side that serves to transfer body fluid to a test field arranged on the membrane.

1 Claim, 2 Drawing Sheets

(56) References Cited

U.S. PATENT DOCUMENTS

| | | | | |
|---|---|---|---|---|
| 6,306,152 B1* | 10/2001 | Verdonk | A61B 5/1411 | 606/182 |
| 6,459,917 B1* | 10/2002 | Gowda | A61B 5/1411 | 600/345 |
| 7,708,703 B2* | 5/2010 | Raney | A61B 5/1411 | 600/573 |
| 2002/0103499 A1* | 8/2002 | Perez | A61B 5/1411 | 606/182 |
| 2003/0059350 A1 | 3/2003 | Sacherer | | |
| 2003/0060730 A1* | 3/2003 | Perez | A61B 5/1411 | 600/576 |
| 2003/0199893 A1* | 10/2003 | Boecker | A61B 5/1411 | 606/181 |
| 2003/0199910 A1* | 10/2003 | Boecker | A61B 5/1411 | 606/181 |
| 2003/0212346 A1* | 11/2003 | Yuzhakov | A61B 5/15146 | 600/584 |
| 2004/0116829 A1* | 6/2004 | Raney | A61B 5/1411 | 600/573 |
| 2005/0038357 A1* | 2/2005 | Hartstein | A61B 5/1411 | 600/583 |
| 2005/0061700 A1* | 3/2005 | Windsmith | A61B 5/1411 | 206/438 |
| 2006/0200044 A1* | 9/2006 | Freeman | A61B 5/1411 | 600/583 |
| 2007/0016103 A1* | 1/2007 | Calasso | A61B 5/1411 | 600/583 |
| 2007/0031283 A1* | 2/2007 | Davis | A61B 5/14546 | 422/400 |
| 2007/0123802 A1* | 5/2007 | Freeman | A61B 5/1411 | 600/583 |
| 2007/0232956 A1* | 10/2007 | Harman | A61B 5/1411 | 600/573 |
| 2008/0021492 A1* | 1/2008 | Freeman | A61B 5/1411 | 606/181 |
| 2008/0097244 A1 | 4/2008 | Amitz | | |
| 2009/0010802 A1 | 1/2009 | Joseph et al. | | |
| 2009/0149725 A1* | 6/2009 | Gofman | A61B 5/1411 | 600/309 |
| 2010/0145228 A1* | 6/2010 | Roe | A61B 5/1411 | 600/583 |

FOREIGN PATENT DOCUMENTS

| | | |
|---|---|---|
| EP | 2039607 A1 | 3/2009 |
| WO | 0166010 A1 | 9/2001 |
| WO | 2009037192 A1 | 3/2009 |

\* cited by examiner

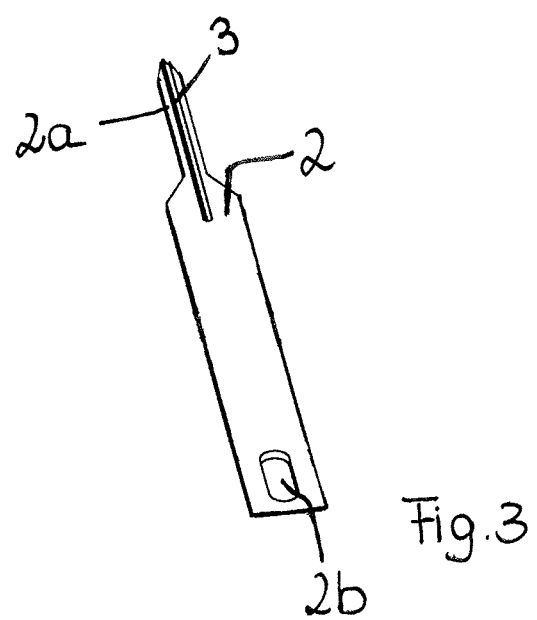

LANCET MAGAZINE AND METHOD FOR THE PRODUCTION THEREOF

This application is a continuation of International Application PCT/EP2011/001846, filed Apr. 13, 2011, which claims priority to EP Application No. 10004776.0, filed May 6, 2010, both of which are hereby incorporated by reference in their entirety.

BACKGROUND

The present disclosure is based on a lancet magazine. Such a lancet magazine has a housing and a plurality of lancets each of which is enclosed in a sterile chamber of the housing, wherein the chambers each comprise a puncturing opening which is closed with a foil, for example made of plastic, metal or paper. Such a lancet magazine is, for example, known from EP 0 951 939 B1.

In certain known lancet magazines, the lancets are arranged in housing chambers along with a drying agent, with the openings of said housing chambers being sealed with a foil in a moisture-proof manner. In such a magazine, lancets are sterilized by exposure to intense radiation or are introduced into the magazine under sterile conditions with a great deal of expense and effort, with the magazine being sealed thereafter.

Lancet magazines are required for lancet devices which are used to collect body fluid samples, normally blood and/or interstitial fluid, for the measurement of an analyte concentration. Such lancet devices and lancet magazines suitable for the same are, for example, required by diabetics who have to check their blood glucose level several times a day.

Lancet magazines each contain a plurality of lancets in sterile packaging, which can be used with a lancet device one after the other. Lancet magazines provide high user convenience because they can be easily inserted into a lancet device and have to be replaced only after all lancets contained therein have been used.

In addition to simple lancets which merely serve to induce a puncture wound, there are also known lancets which comprise a sample receiving device, for example a capillary channel. Such lancets provide particularly high user convenience because a separate action on the user's part for receiving a sample is not required. When punctured into the body of a patient, such a lancet automatically receives a body fluid sample which can then be examined.

An aspect of the present disclosure is to show a way how the costs for the production of a lancet magazine with lancets packed therein in sterile manner can be reduced. Furthermore, the embodiments of the present disclosure are intended to make it easier to receive and examine a body fluid sample.

SUMMARY

Within the scope of the present disclosure, it has been realized that a moisture-proof packaging is not required for storing lancets in a magazine in sterile manner. The lancets of a lancet magazine according to the present disclosure are arranged in chambers which are closed with a membrane that is permeable to gas and moisture. Although, under production, storage and utilization conditions, the membrane of a lancet magazine according to the present disclosure prevents causative organisms from penetrating, it is nevertheless permeable to a sterilizing gas, for example hot water vapor and/or ethylene oxide.

Normally, production, storage and utilization conditions are characterized in that the membrane is not exposed to any fluids before a body fluid sample is collected and, in consequence of the relatively small volume of the magazine chamber, is only exposed to low gas streams after sterilization. This ensures that even particles, for example microorganisms, that are smaller than the largest pores of the membrane, can be reliably separated. Normally, the rule of thumb that can apply for the separation of particles from a slow gas stream is that the only particles which can pass through the membrane are particles with a diameter of less than a tenth of the relevant pore diameter.

The pores form channels that extend through the membrane. Therein, the relevant pore diameter of the membrane is determined by the channel diameter at its narrowest point. The channel which has the largest diameter at its narrowest point determines the permeability of the membrane. This diameter is the relevant pore diameter.

In one embodiment of the present disclosure, the membrane has continuous pores with a relevant diameter of no more than 5 µm. In another embodiment, the membrane has continuous pores with a relevant diameter of no more than 2 µm. Such a membrane can, therefore, retain particles being 0.5 µm and 0.2 µm, respectively, in size. Normally, the size of microorganisms is in excess thereof, for which reason they can be retained by such a membrane. On their coarsely pored side, asymmetric membranes may absolutely comprise larger pores which, however, become narrower towards the fine pored side. In asymmetric membranes, the relevant diameter for continuous pores is, therefore, the pore diameter on the fine pored side.

While, in lancet magazines that are sealed in a moisture-proof manner, sterilization of the lancets contained therein can only be achieved by radiation with considerable expense and effort, lancets in a lancet magazine according to the present disclosure can be sterilized at significantly reduced costs by introducing a sterilizing gas through the membrane and into the magazine chamber. This can be achieved with low expense and effort, for example by exposing lancet magazines to 121° C. hot water vapor for 20 minutes.

Gas-permeable materials can, for example, be produced from a fiber material. Suitable are, in particular, nonwoven materials that are made of plastic fibers. It is, however, also possible to use other porous materials for a gas-permeable membrane, for example open-cell foamed plastics, membranes produced according to a phase inversion method, or the like. Preference is given to hydrophilic membranes.

The lancets of a magazine according to the present disclosure have a sample receiving device, for example one or a plurality of channels for receiving a body fluid sample. In one aspect of the present disclosure, such a channel is designed as a groove, but can also, for example, be a slot. Such sample receiving devices are filled with body fluid by capillary forces when the lancet is punctured into body tissue.

Surprisingly, lancets of a lancet magazine according to the present disclosure allow receiving the sample in a considerably better manner than lancets of equal geometry of the sample receiving device that are disposed in magazines sealed in a moisture-proof manner and sterilized by exposure to radiation. This is attributed to the fact that, in case of sterilization by high-energy radiation, radicals are produced in the plastic of a magazine housing and low-molecular compounds are released which pass over into the gas phase and can deposit on the surface of a lancet in the course of storage time. These deposits seem to have a hydrophobing effect on the surface of a lancet and therefore to make receiving the sample difficult. In a lancet magazine according to the present disclosure, the lancets of which are sterilized by exposure to a sterilizing gas, in particular water vapor, the surface of lancets is, however, not affected.

After sterilization, a test field with analytical reagents for the examination of a body fluid sample is applied onto the gas-permeable membrane. Where commercially available test strips are concerned, suitable analytical reagents are known, for example, for photometric or electrochemical measurement of the concentration of glucose or other medically significant analytes. The risk of sensitive analytical reagents being affected by the sterilization process is excluded according to the present disclosure in that test fields are not attached in a lancet magazine before sterilization is completed.

In a magazine according to the present disclosure, the gas-permeable membrane can, in this manner, be used both as a sterile barrier which prevents germs from penetrating and for transferring a body fluid sample from a lancet to the test field. That is to say that a body fluid sample which has been received by the sample receiving device of a lancet can be transferred to the test field by using a membrane for closing a chamber opening, said membrane being permeable to gas and fluid. To achieve this, it is sufficient to bring the lancet and its sample receiving device into contact with the inner side of the membrane. The body fluid sample can then be delivered through the membrane and to the test field by capillary forces.

There are various alternatives of applying a test field with analytical reagents for the examination of a body fluid sample onto the surface of a membrane. For example, the test field can be formed on a backing film which is placed onto the membrane, with the result that the analytical reagents are arranged between the backing film and the gas-permeable membrane. Another alternative is to apply analytical reagents as a paste directly onto the surface of the membrane and to form a test field on the surface of the membrane in this manner. The analytical reagents can be available as a single layer with a defined composition or as a plurality of layers which differ in their particular compositions and complement one another functionally. For example, one layer of the analytical reagents can form a reflective layer while a layer arranged thereon reveals a coloring which depends on the concentration.

In a magazine according to the present disclosure, the chambers comprise a further opening in addition to the puncturing opening the closure of which is pierced during a puncture, said further opening being closed with a membrane that is permeable to gas and fluid and fulfills a plurality of functions. The membrane allows introducing a sterilizing gas into the chamber for sterilizing the lancet, thereafter serves as a sterile barrier to prevent causative organisms from penetrating into the chamber and, after a puncture, transports a body fluid sample from the sample receiving device of a lancet on one side of the membrane to a test field on the other side of the membrane. So, the membrane has a lower side that faces the lancet and serves to receive body fluid from the sample receiving device and an upper side that serves to transfer body fluid to a test field disposed on the membrane.

Optionally, each magazine chamber additionally has a slide-in opening the closure of which is pierced by a lancet device to trigger a puncture. However, the puncturing opening and the slide-in opening can also be combined to form a single opening which is then also referred to as a puncturing opening to simplify matters.

In one embodiment of the present disclosure, the membrane of a magazine has a pore size that increases in a direction from the interior region of the chamber towards the outside. This allows a particularly good combination of a high-quality fluid transport from the interior region of the chamber to the test field with an impermeability to microorganisms and any causative organisms.

The present disclosure therefore relates to the use of a membrane that is permeable to gas and fluid and closes an opening of a chamber of a lancet magazine to transport a body fluid sample from a lancet on one side of the membrane to a test field on the other side of the membrane.

The present disclosure also relates to a system for the measurement of an analyte concentration of a body fluid sample, said system comprising a lancet device and a lancet magazine that can be inserted into the lancet device. The lancet magazine comprises a housing and contains lancets enclosed in sterile chambers, wherein at least one opening of each chamber containing a lancet is closed with a membrane that is permeable to gas and fluid and carries a test field. The lancet device contains a mechanism in order to initiate a puncturing motion of a lancet and, after a puncture, bring the sample receiving device of a lancet into contact with the inner side of the membrane carrying the test field, with the result that a body fluid sample received by the sample receiving device can be moved to the test field by capillary forces.

As has already been mentioned, each magazine chamber containing a lancet in a lancet magazine according to the present disclosure has at least two, optionally at least three openings, i.e. one puncturing opening the closure of which is pierced by a puncture of the lancet, a further opening which is closed with the membrane that is permeable to fluid and carries the test field and, optionally, also a slide-in opening the closure of which is pierced by a drive mechanism of a lancet device in order to initiate a puncturing motion of a lancet. Optionally, only the further opening is closed with a permeable membrane whereas all further chamber openings are closed with a sealing film that is impermeable to gas. In particular, plastic films, metal foils coated with plastic and metal foils can be used as sealing films.

BRIEF DESCRIPTION OF THE DRAWINGS

Further details and advantages of the present disclosure will be illustrated by means of an illustrative embodiment with reference being made to the accompanying drawings. In the drawings.

FIG. 3 shows a lancet.

DETAILED DESCRIPTION

Figure 1:
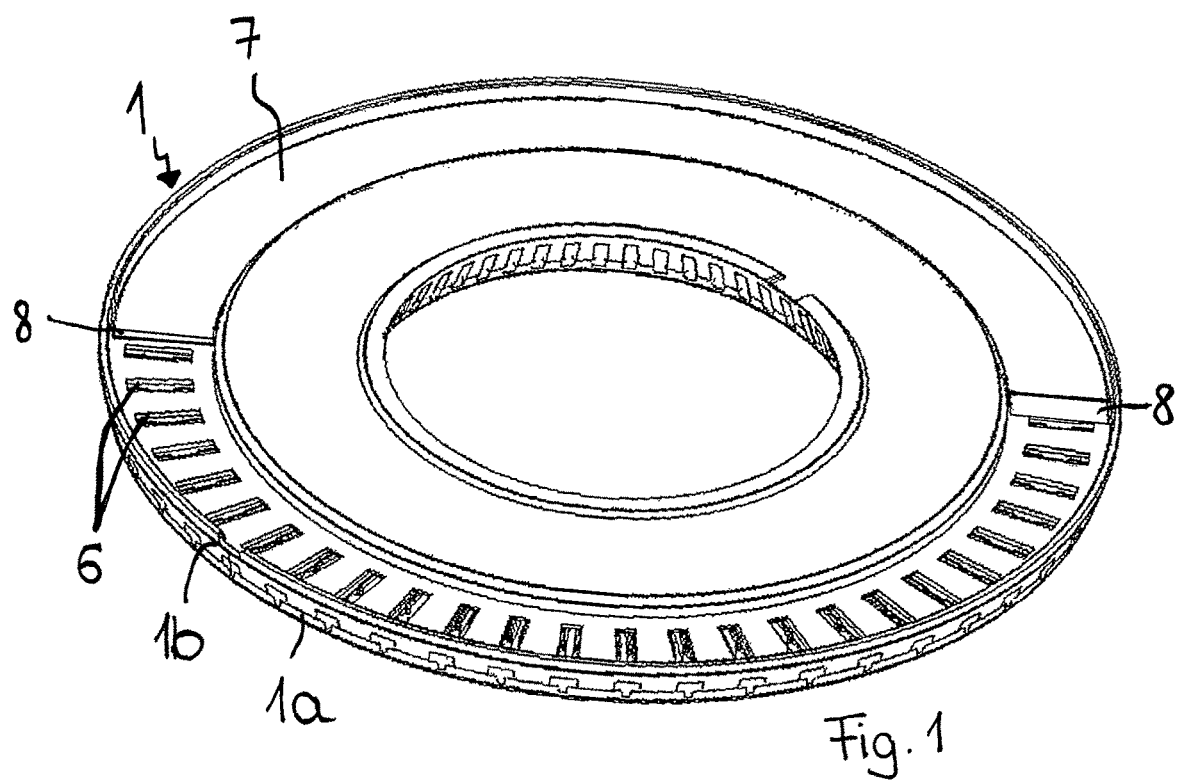
FIG. 1 shows an illustrative embodiment of a lancet magazine according to the present disclosure.
Figure 2:
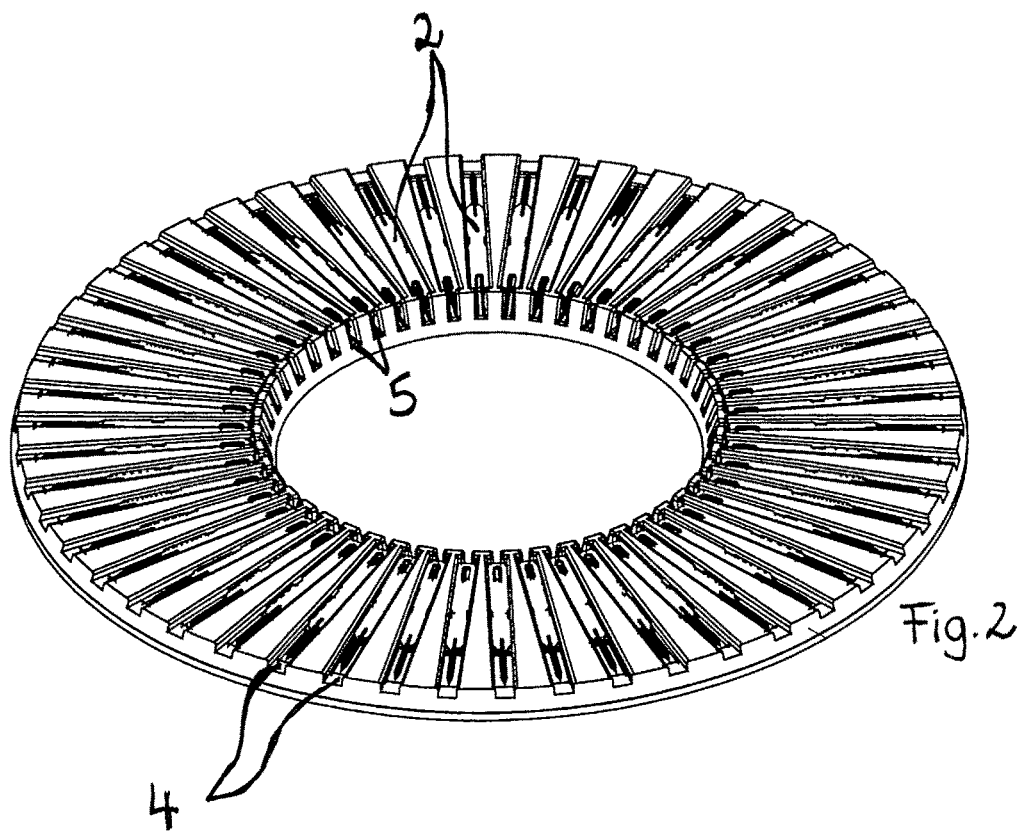
FIG. 2 shows one half of the magazine shown in FIG. 1 with lancets arranged therein.

FIG. 1 shows a lancet magazine with a plastic housing, for example, made of polycarbonate or polysulphone. In the illustrated illustrative embodiment, the housing is joined together from two housing halves 1a, 1b. The lower housing half 1b is shown in FIG. 2. The housing 1 has a plurality of chambers, with a lancet 2 being arranged in each of said chambers.

An illustrative embodiment of a lancet 2 is shown in FIG. 3. The lancet 2 has a sample receiving device 3 which, in the illustrated illustrative embodiment, is designed as a channel, more precisely a groove. During a puncture into the body tissue of a patient, the channel is filled with blood and/or interstitial fluid by capillary forces. A plurality of channels can be provided one beside the other to increase the sample volume received. The sample receiving device 3 can comprise a hydrophilic coating, for example heparin, in order to achieve a better receiving of the sample.

Optionally, the individual chambers of the housing 1 each have at least three openings, i.e. a puncturing opening 4 with the lancet 2 exiting from said puncturing opening 4 during a puncture, a slide-in opening 5 into which a plunger of a lancet device can be pushed in order to push a lancet 2 forward out of the puncturing opening 4 for a puncturing motion and retract it again, as well as a further opening 6 which is covered by a test field 7. FIG. 1 only shows half of the further openings 6 in covered condition in order to give a better view of the structure of the lancet magazine.

The openings 6 are closed with a fluid-permeable membrane 8 on which the test field 7 is disposed. The membrane 8 has a permeability limit of less than 0.5 µm, and optionally 0.2 µm. Particles the size of which is in excess of the permeability limit are retained by the membrane 8, whereas smaller particles can pass through said membrane 8. The pores of the membrane 8 form channels extending through the membrane 8. Therein, the relevant pore size is the maximum diameter of the channels at their narrowest point. Optionally, the relevant pore size of the membrane is no more than 5 µm, and optionally is no more than 2 µm.

Suitable membranes 8 can, for example, consist of fiber material. Apart from paper, materials made of plastic fibers, in particular nonwoven materials, are particularly suitable. DuPont sells a suitable nonwoven material which consists of heat-sealed polyethylene fibers under the trade name of "TYVEC®". As an alternative to fiber materials, use can also be made of other porous materials, for example foamed plastics or membranes produced according to the phase inversion method. A suitable membrane 8 is, for example, sold by Messrs. Pall GmbH, Dreieich, Germany, under the name of BTS 45. Hydrophilic membranes are particularly suitable.

The other chamber openings, i.e. the puncturing opening 4 and the slide-in opening 5 in the illustrated instance, can actually also be closed with a membrane 8 that is permeable to fluid and, therefore, also to gas. Alternatively, however, the openings 4, 5 are closed with a more cost-effective material, i.e. gas-tight foils (not shown). Plastic films, metal foils and plastic-coated metal foils are particularly suitable.

The first step in the production of the magazine shown in FIG. 1 is arranging the lancets 2 in the magazine chambers. Subsequently, the chamber openings 4, 5 and 6 are closed. Thereafter, the lancets 2 are sterilized by introducing a sterilizing gas through the gas-permeable membrane 8 and into the magazine chambers. For example, the closed magazine can be exposed to 121° C. hot water vapor for 20 minutes. To improve the sterilization effect, further sterilizing gases can be admixed to the water vapor. For example, it is also possible to use ethylene oxide as sterilizing gas, in particular according to DIN EN 550 or EN ISO 11135.

The lancets 2 are disposed in the magazine chambers such that they are exposed, which means that they are in contact with the gas contained in the chambers and, therefore, also with the gas introduced for sterilization. The tips of the lancets 2 and a puncture region 2a which is disposed adjacent to the tips and penetrates into the body of a patient during a puncture, optionally, do not have any contact with the magazine housing 1, with the result that the complete surface of the puncture region 2a is in contact with the gas contained in the chambers and, therefore, also with the gas introduced for sterilization. For this reason, the puncture region 2a can be sterilized by exposure to gas in a particularly fast manner. For example, the lancets 2 can be held in the magazine chambers and rest against magazine walls by means of a lancet body adjacent to the puncture region 2a.

After sterilization, a test field 7 with analytical reagents for the examination of a body fluid sample is applied onto the gas-permeable membrane 8. In the presence of an analyte, for example glucose, the analytical reagents initiate a detection reaction which can be evaluated to determine the searched-for analyte concentration. Optionally, use is made of analytical reagents the detection reaction of which causes the test field to change its color, thus allowing a photometric evaluation such as it is customary with commercially available test strips.

The chamber openings 6 can each be closed with individual membrane platelets. It is, however, easier to cover a plurality, optionally all, of the chamber openings 6 with a single piece of membrane 8. In corresponding manner, individual test fields 7 can be applied onto each of the closed chamber openings 6. It is, however easier to cover a backing film, for example made of transparent plastic, with analytical reagents and to place it onto the membrane 8. If use is made of an impermeable backing film, it must be ensured that the reagent layer on the backing film faces the membrane 8. In one embodiment, the reagent layer rests against the membrane 8 and, therefore, has contact therewith, with the result that a body fluid sample can easily pass over from the membrane 8 into the reagent layer.

So, the membrane that is permeable to gas and fluid has a lower side that faces the lancet 2 and serves to receive body fluid from the sample receiving device 3 and an upper side that serves to transfer body fluid to a test field 7 disposed on the membrane 8. Optionally, the pore size on the lower side of the membrane is in excess of that on the upper side. The increased pore size on the lower side facilitates the passover of body fluid from the lancet into the membrane while the reduced pore size on the upper side makes the penetration of microorganisms and other causative organisms more difficult.

In order to allow a good transfer of the sample from the sample receiving device 3 of a lancet 2 through the membrane 8 and to the test field 7 after a lancet puncture, the reagent layer on the backing film should be designed such that it is relatively smooth. In particular, roughness values SRq of less than 3 µm, optionally of less than 2 µm, are advantageous. Roughness values SRmax of less than 30 µm, and optionally of less than 20 µm, are favorable. The specified roughness values SRmax and SRq each refer to measurements with a laser scanning microscope according to DIN EN ISO 25178/(2 and 3) and an adequate image processing filter according to ISO/DIS 16610-21.

The lancet magazine described can be inserted into a magazine compartment of a lancet device that is not shown here, said lancet device comprising a puncturing drive to push a lancet 2 out of the puncturing opening 4 and retract it again. To achieve this, the puncturing drive can comprise a plunger which, while a puncture is made, is pushed into a slide-in opening 5 of a magazine chamber, is coupled to a lancet 2 and pushes the latter out of the puncturing opening. Therein, both a foil closing the slide-in opening 5 and a foil closing the puncturing opening 4 are pierced. In order to facilitate coupling of the puncturing drive to the lancet 2, the latter can comprise a coupling element that is a perforation 2b in the illustrated illustrative embodiment. The puncturing drive has the effect that the sample receiving device 3 of a lancet 2 rests against the membrane 8 at the end of a lancet motion. Once received, a body fluid sample is then received by the membrane 8 by capillary forces and transported therethrough to the test field 7. A suitable puncturing drive can, for example, be implemented as a rotor drive with a link motion. In addition, the lancet device may have a measuring device which, along with test field 7, allows determining a concentration, for example by photometric measurement.

REFERENCE SYMBOLS

1 Housing
1*a* Housing half
1*b* Housing half
2 Lancet
2*a* Puncture region
2*b* Perforation
3 Sample receiving device
4 Puncturing opening
5 Slide-in opening
6 Further openings
7 Test field
8 Membrane

The invention claimed is:

1. A method comprising:
 transporting a body fluid sample from a lancet on one side of a membrane to a test field on the other side of the membrane, the step of transporting comprises:
  contacting the lancet having the body fluid sample with the inner side of the membrane, and
  delivering the body fluid sample through the membrane to the test field by capillary forces;
 wherein the membrane is permeable to gas and fluid and is configured to close an opening of a chamber of a lancet magazine.

* * * * *